US009372135B1

(12) United States Patent
Benner et al.

(10) Patent No.: US 9,372,135 B1
(45) Date of Patent: Jun. 21, 2016

(54) FLUIDICS PLATFORM AND METHOD FOR SAMPLE PREPARATION

(75) Inventors: W. Henry Benner, Danville, CA (US); John M. Dzenitis, Danville, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 956 days.

(21) Appl. No.: 13/228,370

(22) Filed: Sep. 8, 2011

(51) Int. Cl.
*G01N 1/00* (2006.01)
*B01L 3/00* (2006.01)
*G01N 1/40* (2006.01)
*G01N 35/00* (2006.01)

(52) U.S. Cl.
CPC ............ *G01N 1/405* (2013.01); *G01N 35/0098* (2013.01); *B01L 3/5027* (2013.01); *B01L 3/50273* (2013.01); *B01L 3/502761* (2013.01); *B01L 2200/0631* (2013.01); *B01L 2200/0647* (2013.01); *B01L 2200/0668* (2013.01); *B01L 2400/0475* (2013.01); *B01L 2400/0478* (2013.01); *B01L 2400/0605* (2013.01); *G01N 1/40* (2013.01)

(58) Field of Classification Search
CPC ............ B01L 3/5027; B01L 3/50273; B01L 3/502761; B01L 2200/0631; B01L 2200/0647; B01L 2200/0668; B01L 2400/0475; B01L 2400/0478; B01L 2400/0605; G01N 1/40; G01N 1/405; G01N 35/0098
See application file for complete search history.

(56) References Cited

U.S. PATENT DOCUMENTS

| 3,447,479 | A | * | 6/1969 | Rosenberg | .............. | A61M 3/00 417/271 |
| 4,365,153 | A | | 12/1982 | Seigel et al. | | |
| 5,234,809 | A | | 8/1993 | Boom et al. | | |
| 5,647,994 | A | * | 7/1997 | Tuunanen et al. | ............ | 210/695 |
| 6,099,511 | A | * | 8/2000 | Devos et al. | .................. | 604/246 |
| 6,108,611 | A | | 8/2000 | McEwen | | |
| 6,274,869 | B1 | | 8/2001 | Butler | | |
| 6,689,621 | B2 | | 2/2004 | Merten et al. | | |
| 6,693,709 | B2 | | 2/2004 | Wechsler et al. | | |
| 8,203,784 | B2 | | 6/2012 | Nolte et al. | | |
| 8,232,094 | B2 | | 7/2012 | Hasson et al. | | |
| 2002/0045246 | A1 | | 4/2002 | McMillan | | |
| 2002/0064880 | A1 | | 5/2002 | Merten | | |
| 2004/0229349 | A1 | | 11/2004 | Daridon | | |
| 2008/0003649 | A1 | | 1/2008 | Maltezos et al. | | |
| 2008/0057572 | A1 | | 3/2008 | Petersen | | |
| 2009/0130745 | A1 | | 5/2009 | Williams et al. | | |
| 2009/0176314 | A1 | * | 7/2009 | Steinboeck et al. | .......... | 436/174 |

(Continued)

OTHER PUBLICATIONS

Restriction Requirement issued for U.S. Appl. No. 13/228,361, filed Sep. 8, 2011 in the name of Vincent J. Riot mailed on Feb. 4, 2013.

(Continued)

*Primary Examiner* — Christopher A Hixson
(74) *Attorney, Agent, or Firm* — Steinfl & Bruno, LLP

(57) ABSTRACT

Provided herein are fluidics platforms and related methods for performing integrated sample collection and solid-phase extraction of a target component of the sample all in one tube. The fluidics platform comprises a pump, particles for solid-phase extraction and a particle-holding means. The method comprises contacting the sample with one or more reagents in a pump, coupling a particle-holding means to the pump and expelling the waste out of the pump while the particle-holding means retains the particles inside the pump. The fluidics platform and methods herein described allow solid-phase extraction without pipetting and centrifugation.

26 Claims, 6 Drawing Sheets

(56) References Cited

U.S. PATENT DOCUMENTS

| | | | |
|---|---|---|---|
| 2009/0264319 A1* | 10/2009 | Abe et al. | 506/26 |
| 2010/0014157 A1 | 1/2010 | Nolte | |
| 2010/0028980 A1 | 2/2010 | Hasson et al. | |
| 2010/0045246 A1 | 2/2010 | Bryant et al. | |
| 2011/0104747 A1* | 5/2011 | Pollack et al. | 435/40.5 |
| 2011/0224648 A1* | 9/2011 | Secci | 604/518 |
| 2011/0312836 A1 | 12/2011 | Azimi et al. | |

OTHER PUBLICATIONS

Non-Final Office issued for U.S. Appl. No. 13/228,361, filed Sep. 8, 2011in the name of Vincent J. Riot mailed on Nov. 13, 2013.
Non-Final Office Action issued for U.S. Appl. No. 13/228,384, filed Sep. 8, 2011 in the name of Vincent J. Riot mailed on Dec. 4, 2012.
Final Office Action issued for U.S. Appl. No. 13/228,384, filed Sep. 8, 2011 in the name of Vincent J. Riot mailed on Nov. 6, 2013.
Restriction Requirement issued for U.S. Appl. No. 13/228,391, filed Sep. 8, 2011 in the name of Vincent J. Riot mailed on Jul. 26, 2013.
Non-Final Office Action issued for U.S. Appl. No. 13/228,391, filed Sep. 8, 2011 in the name of Vincent J. Riot mailed on Sep. 6, 2013.
Murray, R. et al. Feedback Systems: An Introduction for Scientists and Engineers. Princeton University Press , Princeton, NJ. (2008) Chapter 10, pp. 293-314.
Boom, R. et al., *Rapid and Simple Method for Purification of Nucleic Acids*, J. Clin. Microbial, 1989, 28, pp. 495-503.
Bush, C. et al., *Rapid Isolation of genomic DNA from whole blood to borosilicate particles*, Clin. Chem., 1991, 37, pp. 1060.
Cepheid, *SmartCycler System Brochure*, Retrieved on Jan. 31, 2013.
Smiths Detection, *Bio-Seeq PLUS Brochure*, Retrieved on Jan. 31, 2013.
Smith, M.C. et al., *An integrated portable hand-held analyser for real-time isothermal nucleic acid amplification*, Analytica Chimica Acta, 2007, 598, pp. 286-294.
Roche, *SeptiFast-The Impact of Rapid Results*, 2007.
Cepheid, *GeneXpert System Brochure*, Retrieved on Feb. 12, 2013.
Smith Detection, *Bio-Seeq Product Summary*, 2009.
Promega Technical Manual 284, *Maxwell 16 DNA Purification Kits*, 2012.
Restriction Requirement issued for U.S. Appl. No. 13/228,361, filed Sep. 8, 2011, in the name of Vincent J. Riot, mailed on Feb. 4, 2013.
Non-Final Office Action issued for U.S. Appl. No. 13/228,384, filed Sep. 8, 2011, in the name of Vincent J. Riot, mailed on Dec. 4, 2012.
Notice of Allowance issued for U.S. Appl. No. 13/228,391, filed Sep. 8, 2011 in the name of W. Henry Benner mailed on Apr. 14, 2014.
Non-Final Office issued for U.S. Appl. No. 13/228,384, filed Sep. 8, 2011 in the name of Vincent J. Riot mailed on Jul. 17, 2014.
Advisory Action issued for U.S. Appl. No. 13/228,384, filed Sep. 8, 2011 in the name of Vincent J. Riot mailed on Mar. 12, 2014.
Final Office Action issued for U.S. Appl. No. 13/228,384, filed Sep. 8, 2011 in the name of Vincent J. Riot mailed on Jan. 16, 2015.
Notice of Allowance issued for U.S. Appl. No. 13/228,361, filed Sep. 8, 2011 in the name of Vincent J. Riot mailed on Dec. 5, 2014.
MagneSil® Blood Genomic, MaxYield System, Promega, Technical Bulletin 312. Dec. 2010. Promega_MagneSilBlood_TB312.pdf. 11 pages.
Torres, C. L., et al., (Jun. 16, 2011) "LAVA: An Open-Source Approach to Designing LAMP (Loop-Mediated Isothermal Amplification) DNA Signatures" LLNL-JRNL-413646, torres_dzenitis_LAVA_11nljrn1413646.pdf. 6 pages.
BacT/ALERT Blood Culture Collection, Pocono Health System. 2003. 3 pages. Downloaded from the internet on Jul. 7, 2015: http://www.pmclab.org/manual/17_BacT_Blood_Culture_Collection.pdf.
BacT/Alert 3D User Manual , Jan. 2010, Healthcare Web Site, bioMerieux. 350 pages. Downloaded from the internet on Jul. 7, 2015: http://www.biomeriuex-usa.com/servlets/srt/bio/usa/dynPage?doc=USA_PRD_LST_G_PRD_USA_6.
Advisory Action issued on May 6, 2015 for U.S. Appl. No. 13/228,384, filed Sep. 8, 2011 in the name of Vincent J. Riot, 4 pages.
Non-Final Office Action issued on Jun. 22, 2015 for U.S. Appl. No. 13/228,384, filed Sep. 8, 2011 in the name of Vincent J. Riot, 16 pages.
Final Office Action for U.S. Appl. No. 13/228,384, filed Sep. 8, 2011 on behalf of Vincent J. Riot. Mailed Sep. 8, 2015, 12 pages.
Astrom et al. "Feedback Systems: An introduction for scientists and engineers." Princeton University Press, Princeton, NJ. *Chapter 10, PID Control*, 2009, pp. 293-314.

* cited by examiner

FLUIDICS PLATFORM AND METHOD FOR SAMPLE PREPARATION

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

CROSS REFERENCE TO RELATED APPLICATIONS

This application is related to U.S. Patent Application entitled "SYSTEM AND METHOD FOR MEASURING FLUORESCENCE OF A SAMPLE" having a Ser. No. 13/228,361, filed on even date herewith, to U.S. Patent Application entitled "FLUIDICS CARTRIDGE AND REACTION PLATFORM" Ser. No. 13/228,384, filed on even date herewith, and to U.S. Patent Application entitled "FLUIDICS PLATFORM AND METHOD FOR SAMPLE PREPARATION AND ANALYSIS" Ser. No. 13/228,391, filed on even date herewith, the disclosure of each of which is incorporated herein by reference in its entirety.

FIELD

The present disclosure relates to a fluidics platform and related methods for integrated sample collection, preparation and analysis all in one tube.

BACKGROUND

Many inherently sensitive and specific analytical techniques are greatly degraded by undesirable components in sample matrices. For example, DNA analysis techniques such as PCR and LAMP are typically completely inhibited by components in blood. To overcome this problem, DNA is usually either precipitated, extracted into a different liquid phase, or extracted onto a solid phase and then released to clean liquid.

A convenient method to purify nucleic acid is solid-phase extraction onto paramagnetic silica particles. This allows binding, washing steps, and elution to be conducted without a centrifuge and with a small number of sample transfers. However, the samples still need to be transferred from the initial collection container (such as a blood drawing syringe or vacuum test tube) into a sample preparation tube, and then open transfers of liquid are performed with pipettes or other fluid-moving devices. The initial sample transfer and subsequent open transfers are vulnerable to external contamination, and the fluid metering and transferring equipment can add unwanted complexity. The conventional paramagnetic particle technique involves many pipetting and manipulation steps and is hard to avoid sample-to-sample cross-contamination in reusable fluidics, which would not be acceptable for medical testing due to concerns of false positives.

SUMMARY

Provided herein, are fluidics platforms and related methods for integrated sample collection, preparation and analysis all in one tube.

According to a first aspect, a fluidics platform is described. The fluidics platform comprises a pump, particles and a particle-holding means. The pump comprises a chamber adapted to house a fluidic content, and a plunger adapted to seal inside and slide along a columnar portion of the chamber, wherein the plunger is adapted to draw or expel the fluidic content into or out of the chamber through an opening of the chamber by sliding along the columnar portion of the chamber. The particles are adapted to adsorb a target component of the fluidic content in the chamber and the particle-holding means is adapted to retain the particles inside the chamber.

According to a second aspect, a method for solid-phase extraction of a target component from a sample is described. The method comprises contacting the sample with one or more reagents in a pump, the one or more reagent comprising particles capable of adsorbing the target component of the sample and producing a waste. The method further comprises coupling a particle-holding means to the pump and expelling the waste out of the pump while the particle-holding means retains the particles inside the pump.

The platforms and methods herein described allow in several embodiments integrated sample collection and solid-phase extraction of a target component of the sample in the same container or tube where the sample is originally collected. The platforms and methods herein described allow in several embodiments extraction of a sample component with closed transfer of the sample or other fluidics, thus reducing risks of contamination.

The platforms and methods herein described can be used in connection with applications wherein isolation or purification of a component from sample matrices is desired, including but not limited to medical application, biological analysis and diagnostics including but not limited to clinical applications.

The details of one or more embodiments of the disclosure are set forth in the accompanying drawings and the description below. Other features, objects, and advantages will be apparent from the description and drawings, and from the claims

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

DETAILED DESCRIPTION

Provided herein are fluidics platforms and related methods for integrated sample collection, preparation and analysis all in one tube.

The term "fluidics", "fluidic content", "fluidic input" or "fluidic output" as used herein indicates a substance that continually flows under an applied shear stress. In the sense of the present disclosure, fluid can be liquids, gases, solids, plasma, and colloids, etc. Exemplary types of fluid according to the present disclosure include but are not limited to air, reagent solutions, blood sample, blood serum, blood plasma and fluidic suspension of particles.

Several aspects of the present disclosure relate, at least in part, to solid-phase extraction of a target component of a sample in a same container where the sample is initially drawn. This approach avoids open transferring of the sample or other reagent via conventional liquid transfer methods, such as pipetting, and thus reduces the risk of contamination.

Figure 3:
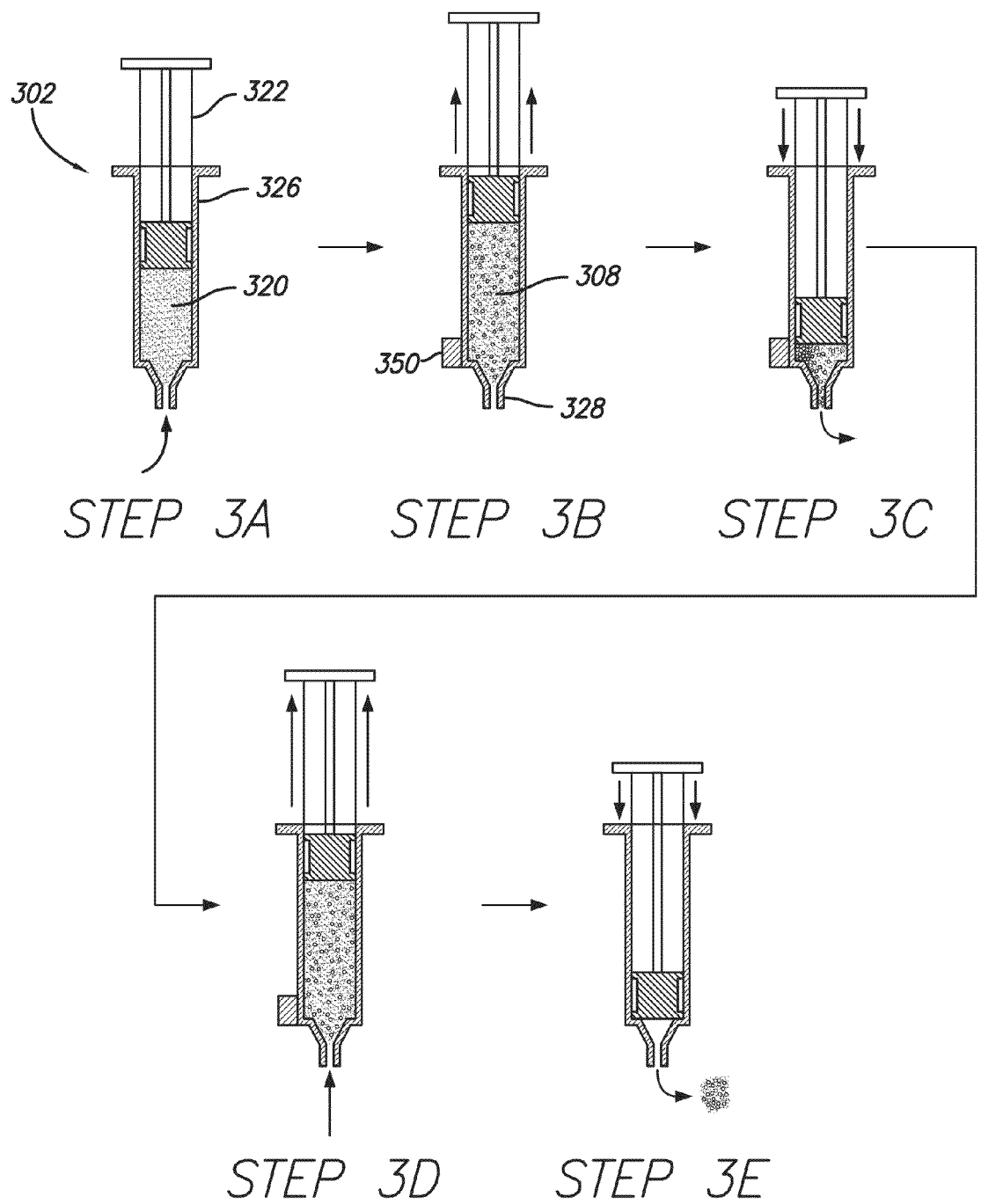
FIG. 3 shows a schematic illustration of an exemplary process of integrated sample collection and preparation using a simple piston pump, magnetic particles and a magnet.

According to a first aspect, a method for solid-phase extraction is described. In several embodiments herein described, solid-phase extraction is performed within a pump (302). As shown in FIG. 3, the pump (302) comprises a chamber (320) for holding the sample and reagents. The pump (302) further comprises a plunger (322), which seals tightly inside the chamber (320) and slides along a columnar portion (326) of the chamber (320) to draw or expel a fluidic content into or out of the chamber (320) through an opening (128).

Also shown in FIG. 3 is a schematic illustration of exemplary steps of performing solid-phase extraction of a target component from a sample. The sample is first loaded into the chamber (320) by drawing the plunger (322) (3A), then one or more reagents are loaded into the chamber to be contacted with the sample (3B). The reagents comprise micro-particles that are capable of adsorbing the target component. The reagents may also prepare the sample into a condition suitable for adsorption of the target component by the particles (308). After contacting the sample with the reagents and particles (308), a particle-holding means (350) is coupled to the pump (302) (3B). The particle-holding means (350) is adapted to retain the particles (308) and the adsorbed target component inside the chamber (320), while the residual of reagent and/or sample is expelled out of the chamber (320) by depressing the plunger (322) (3C).

In some embodiments, the extraction process further comprises agitating the contacted sample and the reagents to allow preparation of the sample into a condition suitable for adsorbing the target component of the sample by the particles (see Example 1).

In some embodiments, the extraction process further comprises washing the retained particles and the extracted component. In particular, a washing buffer is drawn into the chamber (320), and the particles are re-suspended in the washing buffer (1D). After one or more rounds of wash, the particles carrying the extracted component may be expelled out of the chamber (320) for subsequent use or analysis (3E) (see Example 1).

In some embodiments, the extraction process may further comprise drying the retained particles and the extracted component. In some embodiments, the extraction process may further comprise eluting the adsorbed component of the sample off the retained particles. In particular, elution buffer can be drawn into the pump and the particles are re-suspended in the elution buffer until the adsorbed component is released into the elution buffer. Then the elution buffer carrying the target component is expelled out of the pump (302) while the particles are retained in the pump by the particle-holding means (350) (see Example 1).

In some embodiments, the particles (308) are magnetic beads. Accordingly, in those embodiments, as shown in FIG. 3, the particle-holding means comprises a magnet (350), and coupling the particle-holding means is performed by placing the magnet (350) in close proximity to the chamber (320) where the magnetic beads are contained, thus allowing attraction of the beads to the magnet while residual of the reagent and/or sample are expelled out of the chamber (320).

Figure 4:
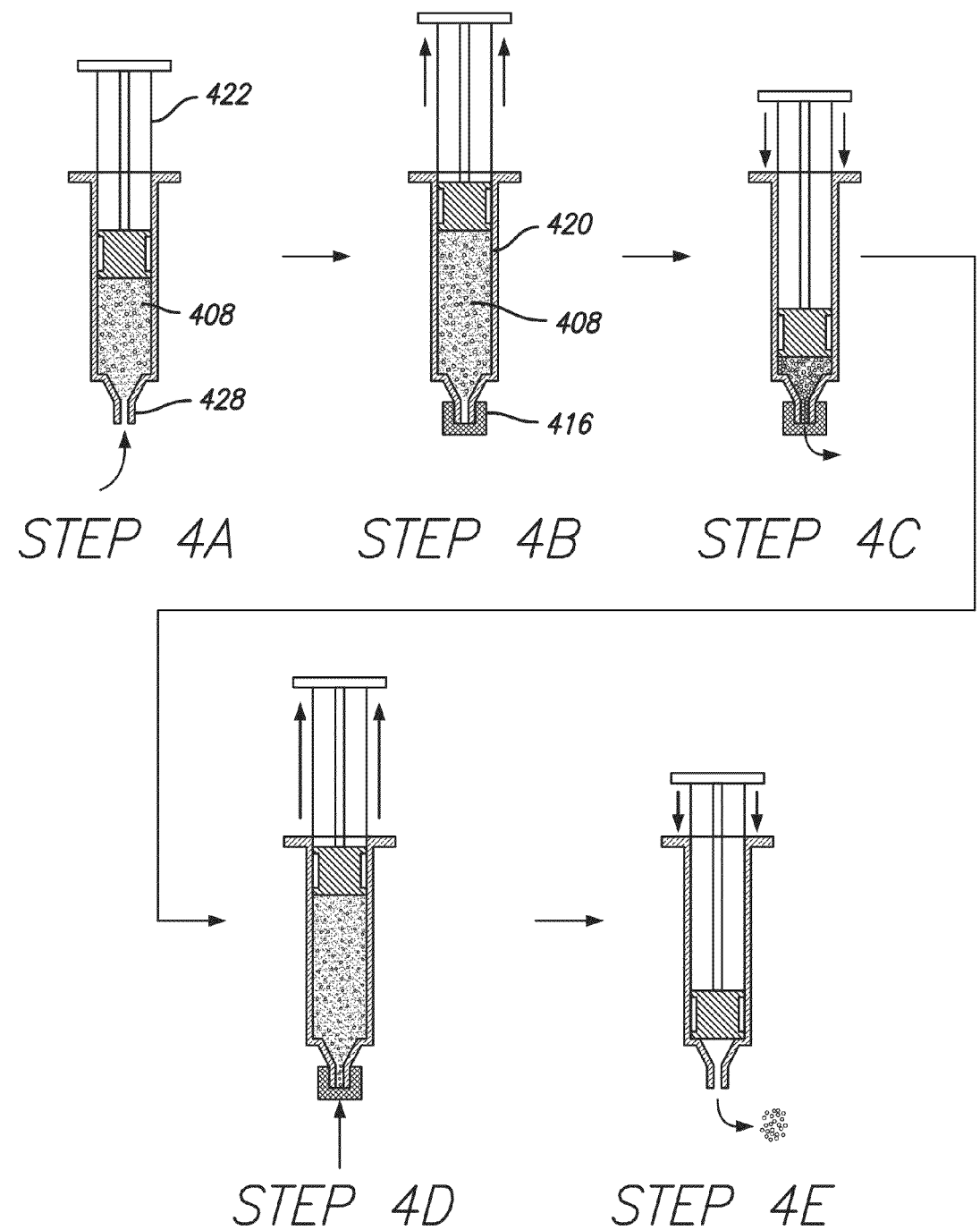
FIG. 4 shows a schematic illustration of an exemplary process of integrated sample collection and preparation using a simple piston pump, particles and a size-differentiating filter.

Alternatively, in some embodiments as shown in FIG. 4, the particle-holding means comprises a size-differentiating filter (416), and coupling the particle-holding means is performed by attaching the size-differentiating filter (416) to an opening (428) of the chamber (420). When the plunger (422) is depressed, (4C), the size-differentiating filter (416) lets the residual of reagent and/or sample pass through but retains the particles (408).

In some embodiments, the sample is a blood sample, and the pump is a hypodermic syringe into which the blood sample was initially drawn.

Figure 2:
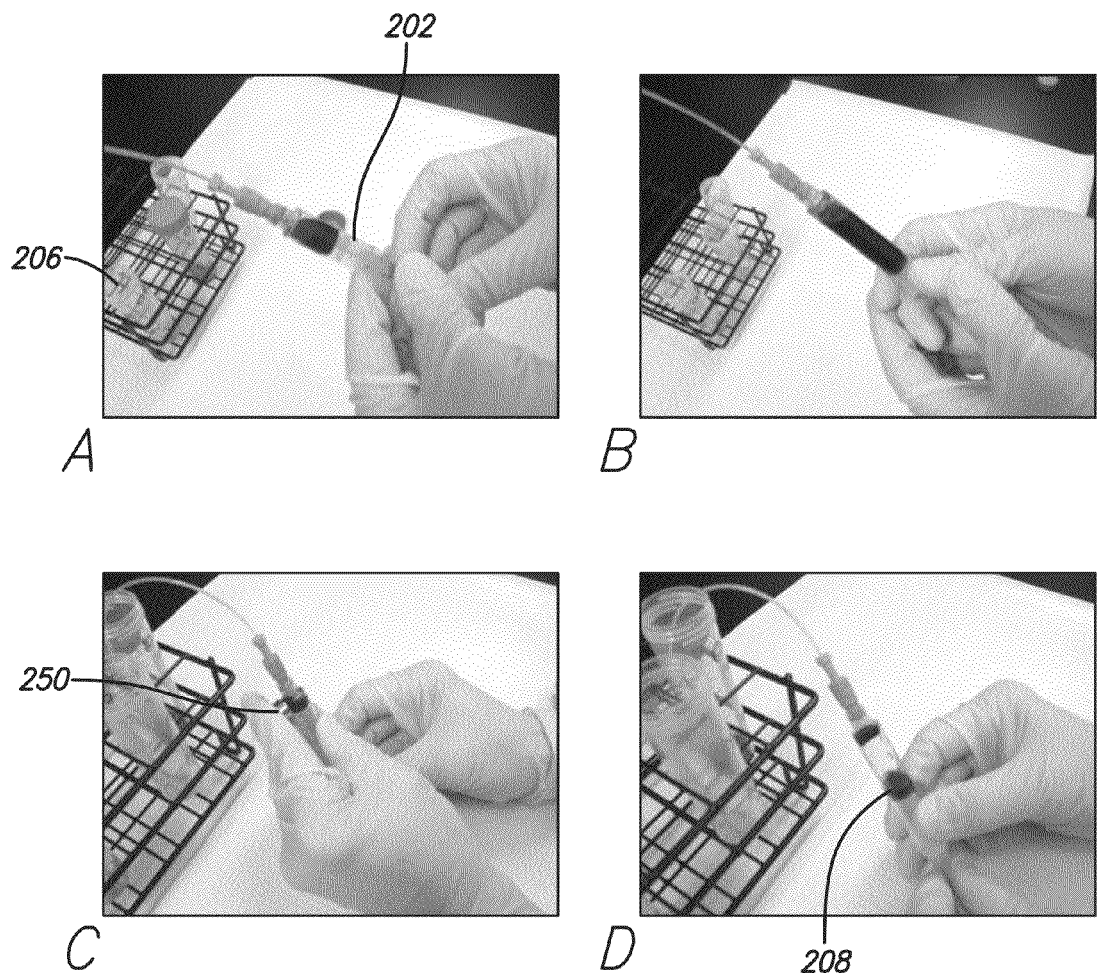
FIG. 2 shows a user manually prototyping a process of integrated sample collection and preparation using a 5-ml syringe, several reagent reservoirs, magnetic particles and a magnet.

FIG. 2 shows steps in the process of manually performing solid-phase extraction using a disposable hypodermic syringe (202), magnetic particles (208), a magnet (250) and several reservoirs (206). In particular, Panel A shows drawing 1 mL whole blood sample into the syringe. Panel B shows drawing blood lysis buffer and magnetic particles for extraction nucleic acids into the syringe (202). Panel C shows attaching a magnet (250) in contact with the syringe (202). After the liquid is expelled from the syringe, the magnetic particles (208) carrying nucleic acids are retained in the syringe (202). They appear as a dark ring near the exit to the syringe in Panel D.

Figure 1:
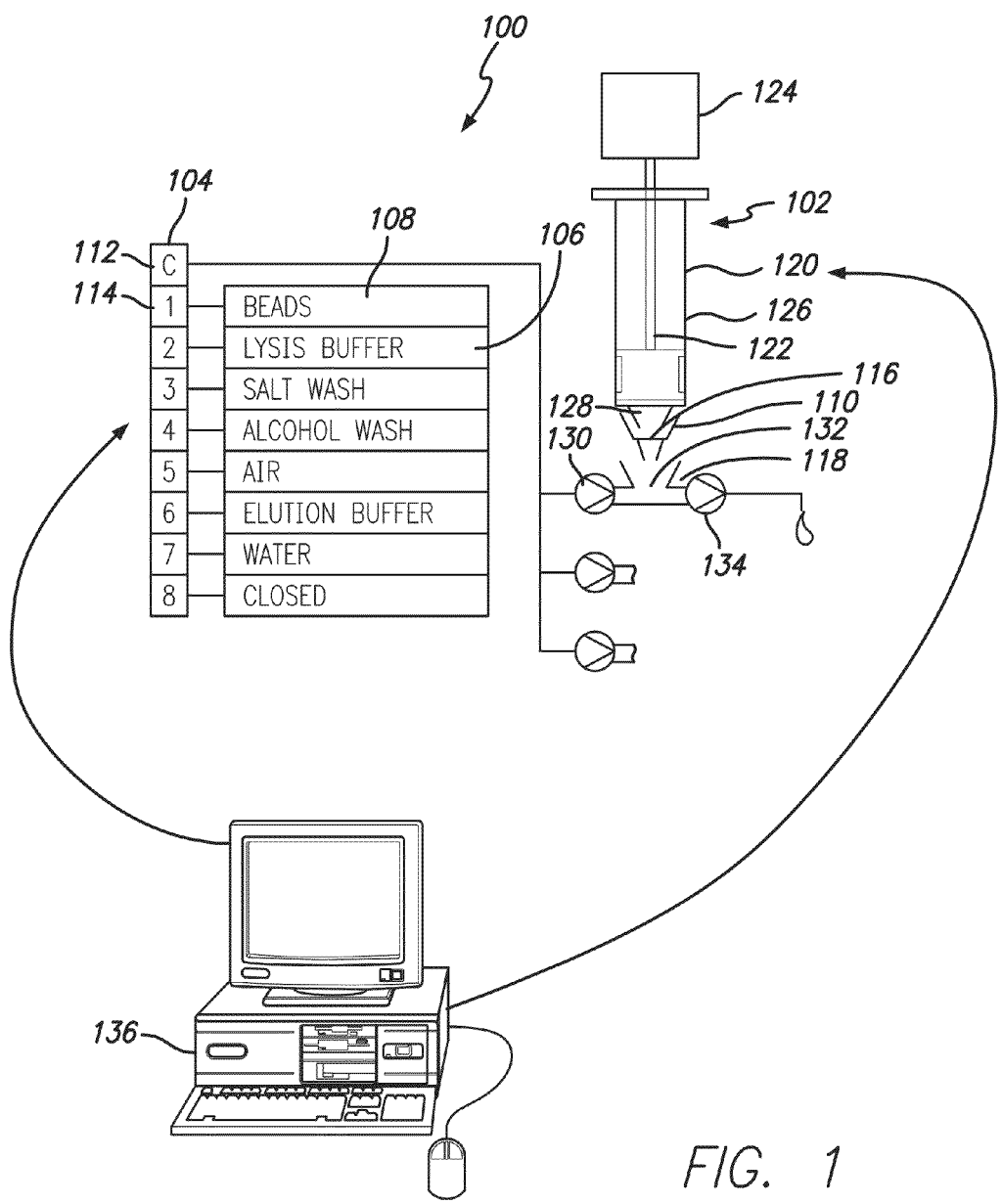
FIG. 1 shows a schematic illustration of connection between components of a fluidics platform according to several embodiments herein described, including a simple piston pump, a pump actuator, a size-differentiating filter, a two-way check valve and a multiport valve.

According to a second aspect, a fluidics platform is described. The platform comprises a pump (102), particles (108) and particle-holding means (110). As shown in FIG. 1, The pump (102) comprises a chamber (120) adapted to house a fluidic content, and a plunger (122) with an air tight seal which fits inside and slides along a columnar portion (126) of the chamber (120), wherein the plunger (122) is adapted to draw or expel the fluidic content into or out of the chamber (120) through an opening (128) of the chamber by sliding along the columnar portion (126) of the chamber. The particles (108) are adapted to adsorb a target component of the fluidic content in the chamber (120). The particle holding means (110) is adapted to retain the particles (108) inside the chamber (120).

As also shown in FIG. 1, in some embodiments, the fluidics platform (100) further comprises a check valve (118). The check valve (118) is coupled to the opening (128) of the pump (102) through a chamber port (132). The check valve (118) further comprises an inlet port (130) adapted to receive a fluidic input when the plunger (122) draws and an outlet port (132) adapted to vent a fluidic output from the chamber (120) when the plunger (122) expels.

As also shown in FIG. 1, in some embodiments, the fluidics platform (100) further comprises a multiport valve (104) and a plurality of reservoirs (106). The multiport valve (104) comprises a common port (104) coupled to the inlet port (130) of the check valve (118). The multiport valve (104) also comprises a plurality of branch ports (114) each coupled to one of the reservoirs (106). The common port (104) is switchably coupled to one of the branch ports (114) at a time. When the plunger (122) draws, the multiport valve (104) draws the fluidic input from a user selected reservoir (106) through a corresponding branch port (114) coupled to the reservoir and through the common port (104), and delivers the fluidic input into the inlet port (130) of the check valve (118).

The plurality of reservoirs (106) as shown in FIG. 1, may comprise the particles for solid-phase extraction, such as a fluidic suspension of magnetic beads (108), reagents adapted to prepare the sample for solid-phase extraction, such as lysis buffer, reagents adapted to wash the particle and extracted component, such as a salt solution and/or an alcohol solution, reagents adapted to elute the extracted component off the particle, such as elution buffer, and other components, such as a connection to a heated air supply for air-drying the particle and extracted component and water for cleaning the fluidic paths of the platform.

As also shown in FIG. 1, in some embodiments, the pump (102) is removably coupled to the chamber port (132) of the check valve (118). Also, in some embodiments, the pump (102) may be a disposable syringe.

In some embodiments, the particle-holding means (110) comprises a size-differentiating filter (116). In other embodiments, the particles are magnetic beads, and the particle-holding means comprises a magnet (see 750 in FIG. 7).

In some embodiments, the fluidics platform (100) is adapted to extract a target component from multiple samples simultaneously. Particularly, as shown in FIG. 1, the platform (100) may comprise more than one check valves (118) and pumps (102). The check valves (118) simultaneously connect to the common port (112) of the multiport valve (104) through a manifold tube (138), and each of the check valves (118) is coupled to a pump (102).

In some embodiments, the fluidics platform (100) further comprises a plunger actuator (124), which is adapted to slide the plunger (122) along the columnar portion (126) of the chamber (120). The sliding action may be accomplished by means of a motor and screw-drive mechanism.

In some embodiments, the plunger actuator (124) may form part of a syringe pump. In some embodiments, wherein the platform (100) have a plurality of pumps (102), the plungers (122) associated with the plurality of pumps (102) may be actuated in parallel by the same actuator (124).

Figure 5:
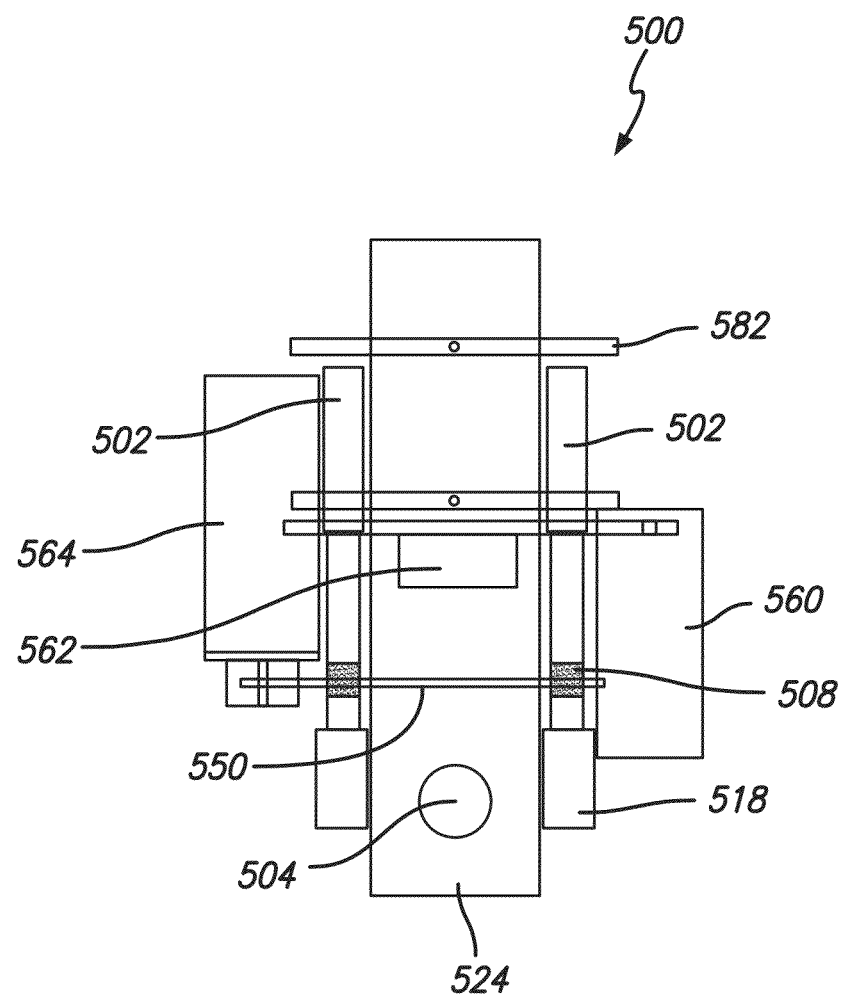
FIG. 5 shows an exemplary mechanical layout of a fluidics platform according several embodiments herein described.

FIG. 5 shows exemplary mechanical layout of the fluidics platform (100) according several embodiments herein described. In particular, according to this embodiment, the platform (100) comprises two or more pumps (502) each coupled to a check valve (518). The platform comprises an actuator (524) adapted to actuate the plungers of the pumps (502) simultaneously. The plunger actuator (524) comprises a plunger holder (582). The platform also comprises a multiport valve (504) for selective reagent pumping. The platform further comprises a magnetic bar (550) which is operated by a magnet actuator (564). The magnet actuator (564) may position the magnetic bar (550) in a position close to both pumps (502) simultaneously to allow attraction of magnetic beads (508), such as the position as shown in the figure, or move the bar (550) away from the pumps (502), such a position is not shown in the figure.

Figure 6:
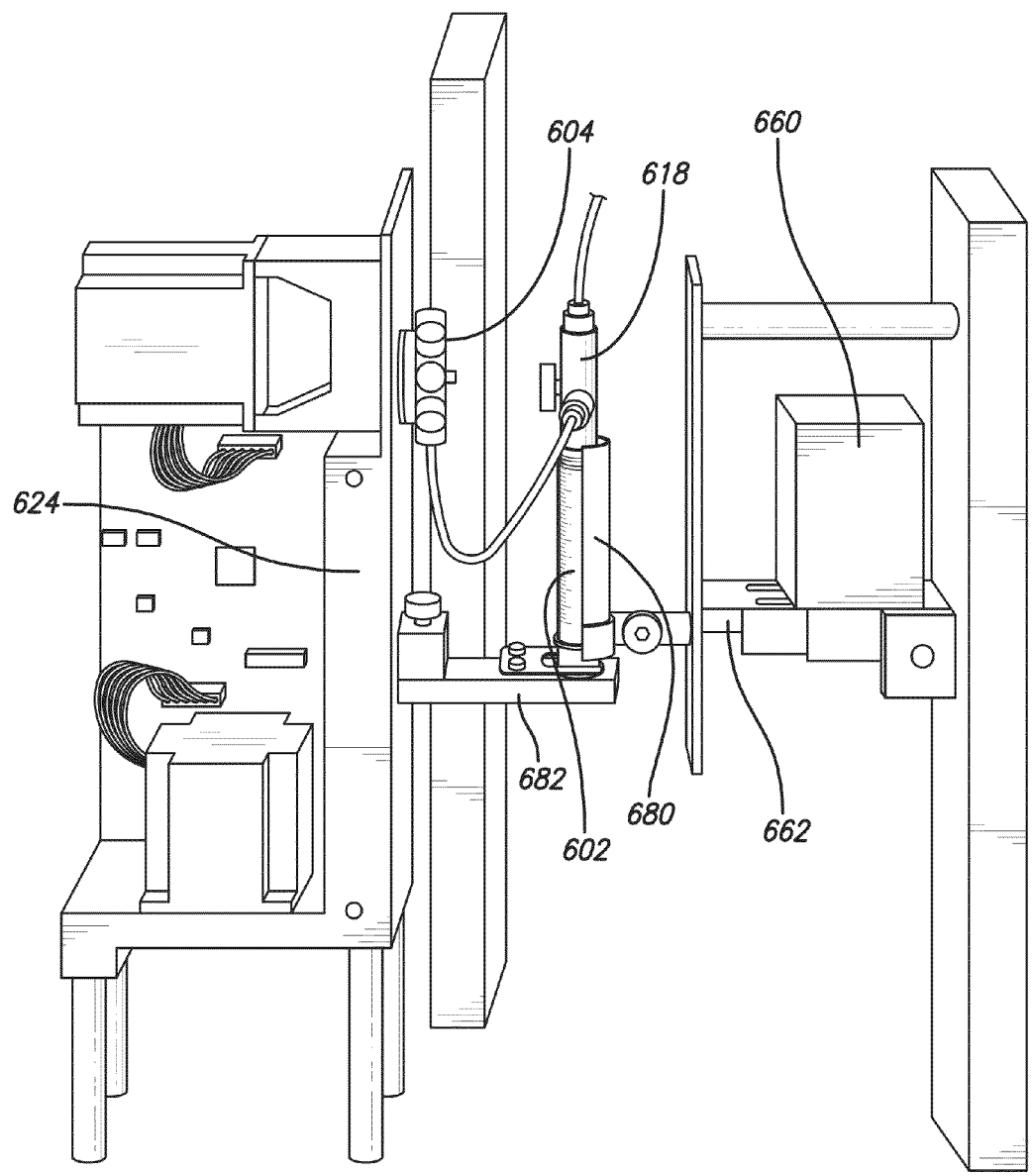
FIG. 6 shows a schematic illustration of a fluidics platform according to an embodiment herein described.

FIG. 6 shows a schematic illustration of a fluidics platform (100) according to an embodiment herein described. The fluidics platform (100) comprises a syringe (602), a plunger actuator (624), of which a plunger holder (682) is shown. The platform (100) also comprises a heater (680) adapted to heat the fluidic content of the syringe (602). The platform also comprises a shaker, of which both a shaker motor (660) and a shaker slider (662) are shown. The shaker is adapted to agitate the fluidic content of the syringe (602). The shake may also agitate fluidic content within one or more of the reservoirs (606).

In some embodiments, the fluidics platform (100) may be coupled with a reaction and/or detection unit, so that the extracted component prepared by the platform (100) may be analyzed. One exemplary embodiment of the reaction and/or detection is described in a related application titled "A FLUIDICS CARTRIDGE AND REACTION PLATFORM", filed on even date herewith, Ser. No. 13/228,384, herein incorporated by reference in its entirety.

In some embodiments, the fluidics platform (100) may be manually operated by a user. For example, the user may manually operate the pump (102) to collect a sample, and to draw or expel suitable amounts of reagents. The user may manually switch the multiport valve (104) to selectively connect the main port (112) to one of the branch ports (114). The user may also manually couple or uncouple the particle-holding means (110) with the pump (102). Manual operation may be desired at the point of care or when no electrical power is available, such as under a disastrous condition.

In some embodiment, the fluidics platform (100) further comprises a computer (136) adapted to operate the fluidics platform (100). In particular, the computer (136) may control the switching of the common port (104) and selectively couple the common port (104) to one of the branch ports (114). The computer may also provide control of the plunger actuator (124), the magnet actuator (564), the shaker (560, 562) and the heater (680). In addition, the computer (140) may provide programs for automated analysis procedures and customized analysis programs. These programs specify analysis parameters such as sequences of reagents to be used, flow rates, sample or reagent volume, reaction temperature, mixture time, reaction time, detection mechanisms, etc. A user of the platform may select one of the pre-set programs or create a customized program to and operate the fluidics platform for automated, reagent/sample handling, sample processing, reaction and detection.

In some embodiments, the fluidics platform further comprises a mechanism for liquid-phase extraction of a target component from a sample. At least two reagents are drawn into the chamber of the pump and mixed with a sample also drawn into the chamber. The target component has a higher solubility in at least one of the reagents which is adapted to extract and dissolve a significant percentage of the target component from the sample. The reagents are also capable of forming at least two immiscible phases, with one phase comprising the extracted target component and the other phase comprising a waste. The position of the pump is then adjusted to arrange the opening of the chamber close to the waste phase, so that the waste phase can be expelled out of the chamber while the phase comprising the extracted component is retained in the chamber.

EXAMPLES

The fluidics platform and related methods herein disclosed are further illustrated in the following examples, which are provided by way of illustration and are not intended to be limiting.

Example 1

Solid-Phase Extraction of Nucleic Acid from Whole Blood Sample

Load Samples.

To extract nucleic acid from whole blood, 1 ml of blood is drawn from a reagent vial containing a blood sample into a 5-ml disposable syringe using aseptic technique. A check valve is then attached to the syringe and the syringe is loaded onto the fluidics platform. The above process is then repeated for as many samples as desired for the run. The paramagnetic particle (PMP) slurry reservoir is agitated before PMP were drawn from the reservoir.

Lyse Cells and Nucleic Acid Binding.

Then 0.5 ml of air is drawn into the syringe, followed by 2.4 ml of lysis buffer. The syringe is then agitated for 5 seconds. Then 0.5 mL of PMP slurry is drawn into the syringe, followed by 0.7 mL lysis buffer. Then the syringe is agitated for 5 minutes to allow time for cell lysis and nucleic acid absorption by PMP to complete.

After that, the magnet is moved close to the syringe and held in close proximity of the syringe for 30 seconds to allow attraction of PMPs to the magnet. Then spent sample and lysis buffer mixture is pushed out of the syringe, while PMPs are retained in the syringe by the magnet. Then the magnet was moved away from the syringe.

Wash PMPs.

3.1 ml of lysis buffer is drawn into the syringe, and the syringe is agitated for 30 second to re-suspend and wash the PMPs. Then the magnet is moved close to the syringe and held there for 30 seconds. Then spent lysis buffer is pushed out while the washed PMPs are retained. The lysis buffer washing steps are then repeated for a total of 2 times. Then the magnet is moved away from the syringe.

3.1 mL of salt wash buffer is drawn into the syringe, and the syringe is agitated for 30 seconds to re-suspend and wash the PMPs. The magnet is moved close to the syringe and held there for 30 seconds after which the spent salt wash buffer is pushed out while the PMPs were retained by the magnet. Similarly, the salt washing steps were then repeated a total of 2 times. Then the magnet is moved away from the syringe.

3.1 mL of alcohol wash is drawn into the syringe, and the syringe is agitated for 30 seconds to re-suspend and wash the PMPs. The magnet is moved close to the syringe and held there for 30 seconds after which the spent alcohol wash buffer is pushed out while the PMPs were retained by the magnet. The alcohol washing steps are repeated a total of 2 times. Then the magnet is removed away from the syringe.

Dry PMPs.

The syringe is then heated to 65° C. While the temperature is held constant, 5 mL air was drawn into the syringe, held for 30 seconds, and then pushed out. The steps for Air drying were repeated 10 times for a total drying time of about 5 minutes.

Elute Purified Nucleic Acid.

With the syringe maintained at 65° C., 1 mL elution buffer is drawn into the syringe. The syringe is then agitated for 5 minutes to allow elution to complete.

Recover Final Extract.

The outlet of the syringe is coupled to a 1 mL syringe. The magnet is moved to the sample syringe and held there for 30 seconds before the eluted nucleic acid extract was pushed into the 1 mL syringe, while the PMPs were retained by the magnet. Alternatively, the final eluted material can be pushed into other types of storage chambers or tubes, or directed into a detector cartridge.

The examples set forth above and in the enclosed appendixes herein incorporated by reference in their entirety, are provided to give those of ordinary skill in the art a complete disclosure and description of how to make and use the embodiments of the platform and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the disclosure (including appendices) are indicative of the levels of skill of those skilled in the art to which the disclosure pertains. All references cited in this disclosure (including appendices) are incorporated by reference to the same extent as if each reference had been incorporated by reference in its entirety individually.

The entire disclosure of each document cited (including patents, patent applications, journal articles, abstracts, laboratory manuals, books, or other disclosures) is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

LIST OF REFERENCES

1. Rapid and Simple Method for Purification of Nucleic Acids. Boom, R. et al. J. Clin. Microbial. 1989 28:495-503.
2. Process for Isolating Nucleic Acid. Boom, Adriannse, Kievits, Lens, 1993 U.S. Pat. No. 5,234,809.
3. Rapid isolation of genomic DNA from whole blood to borosilicate particles. Bush, C. and M. Harvey, 1991 Clin. Chem. 37:1060.
4. SmartCycler System Brochure, Cepheid http://www.cepheid.com/media/files/brochures/SC Brochure.pdf
5. Bio-Seeq PLUS brochure, Smiths Detection http://www.smithsdetection.com/eng/Bio-Seeq PLUS.php
6. An integrated portable hand-held analyser for real-time isothermal nucleic acid amplification, M. C. Smith et al. Analytica Chimica Acta, 2007 598: 286-294
7. SeptiFast Brochure, Roche http://molecular.roche.com/commonfiles/media/pdf/51septifast.pdf
8. GeneXpert System Brochure 0112-04, Cepheid http://www.cepheid.com/media/files/brochures/GeneXpert%20Brochure 0112-04.pdf
9. Bio-Seeq Product Summary, Smiths Detection http://www.smithsdetection.com/media/Bioseeq_Ciinical_product_summary021809.pdf
10. Maxwell 16 DNA Purification Kits, Promega Technical Manual 284 Promega_Maxwell_TM284.pdf

What is claimed is:

1. A fluidics platform comprising a pump, particles and a particle-holding means,
   wherein the pump comprises
      a chamber adapted to house a fluidic content; and
      a plunger adapted to seal inside and slide along a columnar portion of the chamber,
      a heater configured to cover a full length of the columnar portion of the chamber, wherein
   the plunger is adapted to draw or expel the fluidic content into or out of the chamber through an opening at the top of the chamber by sliding along the columnar portion of the chamber,
   the particles are adapted to adsorb a target component of the fluidic content in the chamber, the particle-holding means is configured to retain the particles inside the chamber, and to remain stationary relative to the chamber when the fluidic content is expelled from the chamber.

2. The fluidics platform of claim 1, further comprising a check valve, wherein the check valve comprises
an inlet port adapted to receive a fluidic input when the plunger draws;
a chamber port coupled to the opening of the chamber and adapted to allow fluid communication between the check valve and the chamber; and
an outlet port adapted to vent a fluidic output of the chamber when the plunger expels.

3. The fluidics platform of claim 2, further comprising a multiport valve and a plurality of reservoirs,
wherein the multiport valve comprises
a common port coupled to the inlet port of the check valve, and
a plurality of branch ports, each branch port of the plurality of branch ports coupled to one of the plurality of reservoirs,
wherein the common port is switchably coupled to one of the plurality of branch ports at a time, and
wherein, when the plunger draws, the multiport valve is adapted to deliver the fluidic input from a particular reservoir in the plurality of reservoirs, through a branch port coupled thereof and through the common port, into the inlet port of the check valve.

4. The fluidics platform of claim 3, wherein the pump is removably coupled to the chamber port of the check valve.

5. The fluidics platform of claim 3, wherein the pump is a disposable syringe.

6. The fluidics platform of claim 1, wherein the particles are magnetic particles and wherein the particle-holding means comprises a magnet.

7. The fluidics platform of claim 6, wherein the particle-holding means further comprises a magnet actuator adapted to move the magnet close to or away from the fluidic content of the chamber and to keep the magnet stationary relative to the chamber when the fluidic content is expelled from the chamber.

8. The fluidics platform of claim 1, wherein the particle-holding means comprises a size-differentiating filter.

9. The fluidics platform of claim 1, wherein the pump further comprises a plunger actuator adapted to slide the plunger along the columnar portion of the chamber.

10. The fluidics platform of claim 1, further comprising a shaker adapted to agitate the fluidic content of the chamber.

11. The fluidics platform of claim 3, further comprising a shaker adapted to agitate a fluidic content of one or more of the plurality of reservoirs.

12. The fluidics platform of claim 1, further comprising a computer adapted to configure and operate the fluidics platform.

13. A method for solid-phase extraction of a target component from a sample, the method comprising:
contacting the sample with one or more reagents in a pump, the one or more reagent comprising particles capable of adsorbing the target component of the sample and producing a waste, wherein the pump comprises
a chamber adapted to house a fluidic content, the fluidic content comprising the sample and the one or more reagents; and
a plunger adapted to seal inside and slide along a columnar portion of the chamber, wherein the plunger is adapted to draw or expel the fluidic content into or out of the chamber through an opening at the top of the chamber by sliding along the columnar portion of the chamber;
coupling a particle-holding means to the pump, wherein the particle-holding means is adapted to retain the particles inside the chamber; and
expelling the waste out of the pump while the particle-holding means retains the particles inside the pump and remains stationary relative to the chamber, wherein the above steps are devoid of pipetting and centrifugation,
wherein the pump further comprises a heater configured to cover a full length of the columnar portion of the chamber.

14. The method according to claim 13, wherein the one or more reagents are capable of preparing the sample into a condition suitable for absorption of the target component by the particles.

15. The method according to claim 14, further comprising agitating the contacted sample and the one or more reagents to allow preparation of the sample into the suitable condition before coupling the particle-holding means to the pump.

16. The method according to claim 13, further comprising washing the retained beads after the expelling.

17. The method according to claim 13, further comprising drying the retained beads after the expelling.

18. The method according to claim 13, further comprising eluting the adsorbed target component off the beads after the expelling.

19. The method according to claim 13, wherein the pump is a syringe.

20. The fluidics platform of claim 1, wherein the particle-holding means is positioned exterior to the chamber.

21. The fluidics platform of claim 1, wherein the particle-holding means is positioned away from the chamber when the fluidic content is drawn into the chamber.

22. The method of claim 13, further comprising moving the particle-holding means away from the chamber after expelling the waste out of the pump.

23. A fluidics platform comprising a plurality of pumps, particles and a particle holder,
wherein each of the plurality of pumps comprises
a chamber adapted to house a fluidic content; and
a plunger adapted to seal inside and slide along a columnar portion of the chamber,
and wherein
at least one of the pumps further comprises a heater configured to cover a full length of the columnar portion of the chamber,
each plunger is adapted to draw or expel the fluidic content into or out of the respective chamber through an opening at the top of the chamber by sliding along the columnar portion of the chamber,
the particles are adapted to adsorb a target component of the fluidic content in the chamber, and
the particle holder is configured to retain the particles inside the chamber, and to remain stationary relative to the chamber when the fluidic content is expelled from the chamber.

24. The fluidics platform of claim 23, wherein the plurality of pumps further comprises a common plunger actuator adapted to slide the plurality of plungers along each of the columnar portion of the chamber.

25. The fluidics platform of claim 1, wherein the heater is further configured to cover only a partial circumference of the columnar portion of the chamber.

26. The fluidics platform of claim 1, wherein the heater has a half-cylindrical shape.

* * * * *